(12) United States Patent
Ido

(10) Patent No.: US 7,709,016 B2
(45) Date of Patent: May 4, 2010

(54) INSECT PROOF BOARDS

(75) Inventor: Yasuhiro Ido, Nagoya (JP)

(73) Assignee: Nichiha Corporation, Nagoya-shi (JP)

( * ) Notice: Subject to any disclaimer, the term of this patent is extended or adjusted under 35 U.S.C. 154(b) by 428 days.

(21) Appl. No.: 11/509,080

(22) Filed: Aug. 24, 2006

(65) Prior Publication Data

US 2007/0048346 A1     Mar. 1, 2007

(30) Foreign Application Priority Data

Aug. 31, 2005   (JP) .............................. 2005-251072

(51) Int. Cl.
*A01N 25/34* (2006.01)
*A01N 25/00* (2006.01)
*B27K 3/15* (2006.01)

(52) U.S. Cl. ........................ 424/413; 424/405; 428/541

(58) Field of Classification Search ................ 424/724, 424/405, 413; 428/541
See application file for complete search history.

(56) References Cited

U.S. PATENT DOCUMENTS 3,130,122 A * 4/1964 Kuderna et al. ............. 514/490

6,582,732 B1 * 6/2003 Bender et al. ............... 424/641
2005/0126430 A1 * 6/2005 Lightner et al. .......... 106/15.05

FOREIGN PATENT DOCUMENTS

| JP | 11-256076 | 9/1999 |
| JP | 2001-158702 | 6/2001 |
| JP | 2003-127272 | 5/2003 |

\* cited by examiner

*Primary Examiner*—Johann R Richter
*Assistant Examiner*—Danielle Sullivan
(74) *Attorney, Agent, or Firm*—Birch, Stewart, Kolasch & Birch, LLP.

(57) ABSTRACT

The object of the present invention is to impart lasting excellent insect proof property to boards.

According to the present invention, an insecticidal treatment liquid which contains an insecticide in an aqueous dispersion of colloidal silica is applied to the surface of a coat on a substrate applied with coating. Namely, according to the present invention, since a coating composition is not used to fix the insecticide to the surface of the coat, the insecticide is not diluted with a resin in the coating composition.

5 Claims, No Drawings

INSECT PROOF BOARDS

BACKGROUND OF THE INVENTION

1. Field of the Invention

The present invention relates to an insect proof board used as, for example, a building board.

2. Description of the Prior Art

Building boards used for buildings desirably possess insect proof property so as to be not invaded by harmful insects such as termite or the like.

In order to impart insect proof property to boards, there have conventionally been provided a constitution in which a top paint containing an insecticide is lightly applied to the top layer of a colored steel board (for example, JP-A-2003-127272), a constitution in which a coating composition incorporated with colloidal silica, a silane-based water repellent agent, a repellent for ant and the like in an aqueous resin emulsion is applied to a substrate (for example, JP-A-1999-256076), and a constitution in which a liquid insecticide is adsorbed on silica gel particles and is fixed to the surface of a substrate via an adhesive layer (for example, JP-A-2001-158702).

According to the prior art techniques in which an insecticide mixed with a coating composition is applied to a substrate, there has been a problem that the insecticide is diluted with a resin which is a main component of the coating composition, and thus the concentration of the insecticide present on the surface of the coat is low, thereby failing to sufficiently exhibit insecticidal effects of the insecticide.

Furthermore, when an insecticide is mixed with a coating composition, the coating composition after application to the surface of a substrate is usually subjected to heat-drying at a temperature of about 100 to 150° C., whereby the insecticide may be denatured and deteriorated by the heat-drying.

In the constitution in which silica gel particles having a liquid insecticide adsorbed thereon are fixed to the surface of a substrate via an adhesive layer, the silica gel particles are liable to be peeled off from the adhesive layer, and thus it is difficult to provide lasting insecticidal effect.

SUMMARY OF THE INVENTION

In order to solve the above problems, the present invention provides an insect proof board obtained by applying, to the surface of a coat on a substrate applied with coating, an insecticidal treatment liquid which contains an insecticide in an aqueous dispersion of colloidal silica.

Usually, an insecticidal treatment liquid is prepared by adding an insecticide to a dispersion of colloidal silica in a mixed solvent of water and an alcohol. In this case, it is desirable to add a surfactant as a dispersant to the dispersion of colloidal silica in a mixed solvent of water and an alcohol.

EFFECT OF THE INVENTION

[Mode of Action]

Since the insecticidal treatment liquid of the present invention is a treatment liquid in which an insecticide is added to an aqueous dispersion of colloidal silica and does not contain a coating composition which contains a resin as a main component, the insecticide is not diluted with the resin but is firmly fixed to the microscopic concavo-convex surface of the colloidal silica, and the colloidal silica is fixed to the coat on the surface of a substrate via hydrogen bonding.

[Effect]

Accordingly, in the present invention, an insecticide is present at a high concentration on the surface of a coat on the substrate via colloidal silica used as a medium, and thus insecticidal effect of the insecticide is effectively exhibited and a board having a significant insecticidal effect is obtainable even if the insecticide is used in an small amount. In addition, since the insecticide is firmly fixed to the coated surface via colloidal silica used as a medium, lasting insecticidal effect can be obtained.

DETAILED DESCRIPTION OF THE INVENTION

The invention will be explained below in detail.

[Substrate]

The substrate to be applied in the present invention includes cement boards (wood fiber cement boards) incorporated with wood reinforcements such as wood flakes, woody pulp, wood fiber or the like, cement extrusion-molded boards, pulp cement boards, plaster boards, calcium silicate boards, magnesium carbonate boards, plywoods, hardboards, medium density fiber boards, iron plates, metal building boards and the like.

Coating is applied to the surface of the substrate. Usually, as the coating, multi-ply coating including under coating, intermediate coating, top coating and clear coating is applied. It is desirable to use an aqueous emulsion-type coating composition such as a coating composition of an aqueous emulsion of acrylic resin or aqueous emulsion of silicone-acrylic resin for the under coating, intermediate coating, top coating and clear coating. However, a solution-type coating composition such as a clear solution type coating composition of an acrylic resin may be used, and combination of the aqueous emulsion-type coating composition and the solution-type coating composition may be used.

[Insecticidal Treatment Liquid]

The colloidal silica used in the insecticidal treatment liquid of the present invention is such a substance that about 10 primary fine particles each having a particle diameter of 5 to 10 nm have associated to form a secondary fine particle and microscopic concavo-convex pattern is formed on the surface thereof. The colloidal silica may contain slight amounts of other components such as aluminum oxide in addition to silicon oxide.

It is desirable in the present invention to add an alcohol to water used as a dispersion medium of the colloidal silica. The alcohol used in the present invention is desirably a water-soluble alcohol such as methanol, ethanol or isopropanol. The alcohol decreases the surface tension of the insecticidal treatment liquid of the present invention, and increases the affinity of the insecticidal treatment liquid to the underlying coat to enhance wettability of the insecticidal treatment liquid.

It is desirable to add a surfactant as a dispersant to the insecticidal treatment liquid of the present invention. As the surfactant may be used any of usual anionic, nonionic and cationic surfactants. Examples of the anionic surfactant include higher alcohol sulfates (Na salts or amine salts) alkylaryl sulfonates (Na salts or amine salts), alkylnaphthalene sulfonic acid salts (Na salts or amine salts), alkylnaphthalene sulfonate condensates, alkyl phosphates, dialkyl sulfosuccinates, rosin soaps, and fatty acid salts (Na salts or amine salts). Examples of the nonionic surfactant include polyoxyethylene alkyl ethers, polyoxyethylene alkyl phenol ethers, polyoxyethylene alkyl esters, polyoxyethylene alkyl amines, polyoxyethylene alkylol amines, polyoxyethylene alkyl amides, sorbitan alkyl esters, and polyoxyethylene sorbitan alkyl esters. Examples of the cationic surfactant include octadecyl amine acetate, acetates of imidazoline derivatives, polyalkylene polyamine derivatives and their salts, octadecyltrimethyl ammonium chloride, trimethylaminoethylalkyl amide halogenides, alkyl pyridinium sulfates, and alkyltrimethyl ammonium halogenides. A mixture of two or more of the surfactants may be used. These examples do not restrict the invention.

The surfactant, together with the alcohol, lowers the surface tension of the insecticidal treatment liquid of the present invention, favorably disperses the colloidal silica in the insecticidal treatment liquid, and increases the affinity of the insecticidal treatment liquid to the underlying coat.

The insecticidal treatment liquid of the present invention usually contains 0.1 to 2.0% by mass of the colloidal silica, 2 to 10% by mass of the alcohol, 0.01 to 0.25% by mass of the surfactant, and a balance amount of water.

If the alcohol is contained in an amount less than 2% by mass, the wettability of the insecticidal treatment liquid is deteriorated, whereas if it is contained in an amount more than 10% by mass, volatility of the solvent increases to adversely affect the coating operation. If the surfactant is contained in an amount less than 0.01% by mass, surface tension-lowering effect and colloidal silica-dispersing effect become unremarkable, whereas if it is contained in an amount more than 0.25% by mass, the film formed by the insecticidal treatment is adversely affected in terms of strength, water resistance, durability and the like. Thus, it is desirable that the insecticidal treatment liquid has a surface tension not more than 20 dyne/cm at 25° C.

The insecticide to be added to the insecticidal treatment liquid is desirably selected from pyrethroid compounds in view of safety to the human body. Examples of the pyrethroid compounds include permethrin, allethrin, tralomethrin, silafluofen, ethofenprox, phenothrin and the like.

The insecticide is added in an amount of usually about 0.01 to 5% by mass of the insecticidal treatment liquid.

[Application of Insecticidal Treatment Liquid]

After coating the substrate, the coat is usually dried by heating to 100 to 150° C. in the final drying process. After drying the coat by heating, the substrate is allowed to cool at normal temperature. Application of the insecticidal treatment liquid is effected when the temperature of the coat lowered to desirably not higher than 80° C., more desirably not higher than 70° C. At a temperature not higher than such temperature, there will not be danger of denaturation by heat of the insecticide. Although the insecticidal treatment liquid is usually applied by spray coating, well known application methods such as coater coating and roll coating may be used.

The amount of application is not restricted, but is usually such an amount as to give an insecticidal layer in a range of approximately 30 to 80 nm in thickness obtained by applying the insecticidal treatment liquid and then drying.

In the insecticidal treatment liquid, plural primary particles of the colloidal silica are associated and agglomerated to form a secondary particle and thus microscopic concavo-convex pattern is formed on the surface of the particles as described in the above. Therefore, the insecticide is captured by and adsorbed on the microscopic concavo-convex surface of the colloidal silica. It is considered that the colloidal silica which has captured and absorbed the insecticide is fixed to the surface of the coat (clear coat) on the substrate via hydrogen bonding.

In the following, examples are illustrated to explain the present invention more specifically.

The following insecticidal treatment liquids 1 and 2 were prepared.

|  | insecticidal treatment liquid 1 | insecticidal treatment liquid 2 |
|---|---|---|
| Colloidal silica (secondary particle Size: 5 μm) | 2% by mass | 2% by mass |
| Insecticide (permethrin) | 0.2% by mass | 0.02% by mass |
| Ethanol | 4% by mass | 4% by mass |
| Surfactant* | 0.02% by mass | 0.02% by mass |
| Balance | water | water |

*Polyothyethylenealkyl phenol ether

The surface of a wood fiber cement board substrate was subjected to under coating, intermediate coating and top coating with a coating composition of an aqueous emulsion of acrylic resin and to clear coating with an acrylic resin solution-type coating composition, and the substrate was dried by heating to 100 to 110° C. in a heating furnace for 20 minutes.

After drying by heating, the coated substrate was taken out from the heating furnace and allowed to cool at room temperature. When the temperature of the surface of the clear coat lowered to 65° C., insecticidal treatment liquids 1 or 2 was applied thereto by spraying. Then the substrate was left to stand at normal temperature to dry the coat of the insecticidal treatment liquid by the remaining heat of the clear coat. Thus, an insecticidal layer of 50 nm thick was formed to give sample 1 (insecticidal treatment liquid 1) and sample 2 (insecticidal treatment liquid 2).

As comparisons, the following comparative samples were prepared: comparative sample 1 in which an insecticidal treatment liquids was not applied to the coated substrate (untreated sample); comparative sample 2 in which the substrate was coated with a clear coating composition containing 0.2% by mass of permethrin; comparative sample 3 in which permethrin was directly applied to the surface of the coated substrate; and comparative sample 4 in which insecticidal treatment liquid 1 was applied to the coated substrate similarly to sample 1 when the temperature of the surface of the coat was 80° C.

Sustention of harmful insect-avoiding effect was evaluated on samples 1-2 and comparative samples 1-4.

Method of evaluation was pursuant to the test method according to Japan Environmental Sanitation Center.

The harmful insect-avoiding effect of each sample was measured immediately after application and drying of an insecticidal treatment liquid, after leaving the substrate outside for 40 days and after leaving the substrate outside for 6 months. The experiment commenced on May 1, 2004 and ended 6 months after therefrom, i.e. on Nov. 1, 2004.

The results of the avoidance rate thus obtained are shown Table 1.

TABLE 1

|  | Avoidance rate (%) | | |
|---|---|---|---|
|  | Immediately after application | After 40 days | After 6 months |
| Sample 1 | 96.3 | 87.4 | 76.2 |
| Sample 2 | 95.6 | 86.6 | 74.3 |
| Comparative Sample 1 | 0 | 0 | 0 |
| Comparative Sample 2 | 97.9 | 88.6 | 68.4 |

TABLE 1-continued

| | Avoidance rate (%) | | |
|---|---|---|---|
| | Immediately after application | After 40 days | After 6 months |
| Comparative Sample 3 | 100 | 87.4 | 61.4 |
| Comparative Sample 4 | 89.7 | 81.2 | 71.1 |

The avoidance rate (%) was calculated according to the following equation 1:

Avoidance rate (%)=(1−number of insects in a tested sample/number of insects in a control sample*)  [Equation 1]

*control sample: comparative sample 1

Referring to Table 1, it was confirmed that there was no much difference in avoidance rate between samples 1 and 2, and that good insecticidal effect was sustained even after 6 months in both samples. Thus, it was confirmed that there is not much correlation between the amount of an insecticide and insecticidal effect.

With regard to comparative sample 2 in which an insecticide was added to a coating composition, insecticidal effect largely decreased after 6 months. With regard to comparative sample 3 in which an insecticide was directly applied, insecticidal effect more largely decreased after 6 months. With regard to comparative sample 4 in which insecticidal treatment liquid 1 was applied when the temperature of the surface of the coat was 80° C., the insecticide denatured by the heat and thus the insecticidal effect thereof was lower than that of sample 1.

INDUSTRIAL APPLICABILITY

The present invention can provide boards having lasting and effective insecticidal effect, and thus is industrially applicable.

What is claimed is:

1. An insect proof board obtained by applying, to the surface of a coat on a substrate applied with coating, an insecticidal treatment liquid which contains an insecticide in an aqueous dispersion of colloidal silica;
   wherein the insecticide is a pyrethroid compound;
   wherein the colloidal silica comprises about 10 primary fine particles each having a particle diameter of 5 to 10 nm; and
   wherein the insecticidal treatment liquid comprises the insecticide, 0.1 to 2.0% by mass of the colloidal silica, 2 to 10% by mass of an alcohol, 0.01 to 0.25% by mass of a surfactant, and a balance amount of water.

2. The insect proof board according to claim 1, wherein the insecticidal treatment liquid is prepared by adding the insecticide to a dispersion of colloidal silica in a mixed solvent of water and an alcohol.

3. The insect proof board according to claim 2, wherein the dispersion of colloidal silica in the mixed solvent of water and an alcohol is incorporated with a surfactant as a dispersant.

4. The insect proof board according to claim 1, wherein the substrate is a cement board, a cement extrusion-molded board, or a calcium silicate board.

5. The insect proof board according to claim 1, wherein an applied layer of the insecticidal treatment liquid has a thickness of 30 to 80 nm.

* * * * *